(12) United States Patent
Kim et al.

(10) Patent No.: US 10,358,441 B2
(45) Date of Patent: Jul. 23, 2019

(54) PROCESSES FOR THE PREPARATION OF BENZODIAZEPINE DERIVATIVES

(71) Applicant: ENANTA PHARMACEUTICALS, INC., Watertown, MA (US)

(72) Inventors: In Jong Kim, Lexington, MA (US); Jianming Yu, Plainsboro, NJ (US); Thomas P. Blaisdell, Brighton, MA (US); Joseph Panarese, Malden, MA (US); Brian C. Shook, Holliston, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 15/898,387

(22) Filed: Feb. 16, 2018

(65) Prior Publication Data

US 2018/0237425 A1 Aug. 23, 2018

Related U.S. Application Data

(60) Provisional application No. 62/459,955, filed on Feb. 16, 2017, provisional application No. 62/459,953, filed on Feb. 16, 2017.

(51) Int. Cl.
*C07D 413/14* (2006.01)

(52) U.S. Cl.
CPC .................. *C07D 413/14* (2013.01)

(58) Field of Classification Search
CPC ................................................ C07D 413/14
USPC ...................................................... 540/521
See application file for complete search history.

(56) References Cited

U.S. PATENT DOCUMENTS

| | | | |
|---|---|---|---|
| 5,571,809 | A | 11/1996 | Hargrave et al. |
| 7,582,624 | B2 | 9/2009 | Carter et al. |
| 9,732,098 | B2 | 8/2017 | Hunt et al. |
| 9,957,281 | B2 | 5/2018 | Shook et al. |
| 2006/0040923 | A1 | 2/2006 | Carter et al. |
| 2006/0083741 | A1 | 4/2006 | Hoffmann et al. |
| 2007/0142403 | A1 | 6/2007 | Powell et al. |
| 2007/0185094 | A1 | 8/2007 | Lattmann et al. |
| 2007/0185096 | A1 | 8/2007 | Powell et al. |
| 2008/0139536 | A1 | 6/2008 | Dowdell et al. |
| 2009/0274655 | A1 | 11/2009 | Grimes et al. |
| 2010/0015063 | A1 | 1/2010 | Carter et al. |
| 2012/0196846 | A1 | 8/2012 | Mackman et al. |
| 2014/0038947 | A1 | 2/2014 | Glick et al. |
| 2015/0065504 | A1 | 3/2015 | Wang et al. |
| 2015/0299210 | A1 | 10/2015 | Bailey et al. |
| 2017/0022221 | A1 | 1/2017 | Shook et al. |
| 2017/0226127 | A1 | 8/2017 | Estrada et al. |
| 2017/0226129 | A1 | 8/2017 | Yu et al. |
| 2017/0355717 | A1 | 12/2017 | Hunt et al. |
| 2018/0193352 | A1 | 7/2018 | Shook et al. |
| 2018/0237425 | A1 | 8/2018 | Kim et al. |
| 2018/0258102 | A1 | 9/2018 | Shook et al. |

(Continued)

FOREIGN PATENT DOCUMENTS

| | | |
|---|---|---|
| EP | 0703222 A1 | 3/1996 |
| WO | 9308175 A1 | 4/1993 |

(Continued)

OTHER PUBLICATIONS

Carter, et al., "1,4-Benzodiazepines as Inhibitors of Respiratory Syncytial Virus," Journal of Medicinal Chemistry, 49, 2311-2319, 2006.

(Continued)

*Primary Examiner* — Brenda L Coleman
(74) *Attorney, Agent, or Firm* — Edgar W. Harlan; Carolyn S. Elmore, Esq.; Elmore Patent Law Group, P.C.

(57) ABSTRACT

The present invention relates to processes and intermediates useful in the preparation of biologically active molecules, especially in the synthesis of Respiratory Syncytial Virus (RSV) inhibitors. The present invention also relates to processes and intermediates for the preparation of compounds of formula (I):

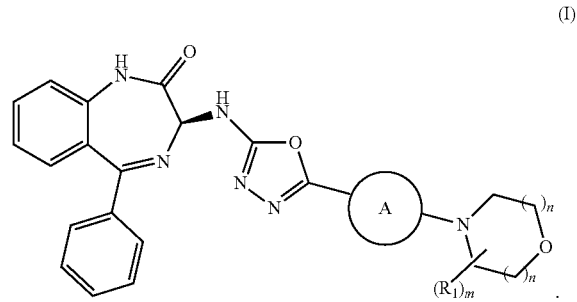

(I)

In particular, the present invention also relates to processes and intermediates for the preparation of compound I-a:

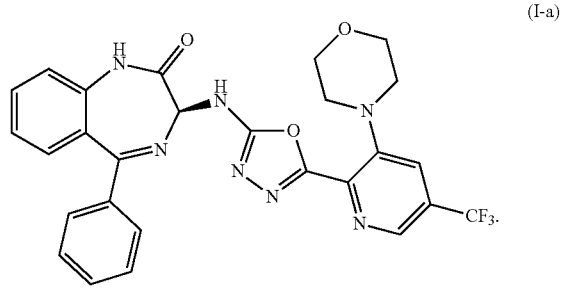

(I-a)

18 Claims, No Drawings

(56) References Cited

U.S. PATENT DOCUMENTS

| | | |
|---|---|---|
| 2018/0354912 A1 | 12/2018 | Or et al. |
| 2019/0002478 A1 | 1/2019 | Kim et al. |
| 2019/0002479 A1 | 1/2019 | Kim et al. |

FOREIGN PATENT DOCUMENTS

| | | |
|---|---|---|
| WO | 2006081389 A1 | 8/2006 |
| WO | 2011005842 A1 | 1/2011 |
| WO | 2014047369 A1 | 3/2014 |
| WO | 2014125444 A1 | 8/2014 |
| WO | 2014184350 A1 | 11/2014 |
| WO | 2016055792 A1 | 4/2016 |
| WO | 2016097761 A1 | 6/2016 |
| WO | 2017123884 A1 | 7/2017 |

OTHER PUBLICATIONS

Henderson, et al., "1,4-Benzodiazepines as Inhibitors of Respiratory Syncytial Virus. The Indentification of a Clinical Candidate," Journal of Medicinal Chemistry, 50, 1685-1692, 2007.
Xiong, et al., "Discover of a potent respiratory syncytial virus RNA polymerase inhibitor," Bioorganic & Medicinal Chemistry Letters, 23:6789-6793, 2013.
Peesapati, et al. (Document No. 120:244848) retrieved from STN; entered in STN on May 14, 1994.
U.S. Appl. No. 15/914,016, filed Mar. 7, 2018.
Respiratory syncytial virus (RSV) [online], retrieved from from internet on Jun. 25, 2017.; URL http://www.mayoclinic.org/diseases-condiitons/respiratory-syncytial-virus/basics/prevention.
Albright, et al. (Document No. 130:153583) retrieved from STN; entered in STN on Feb. 16, 1999.
Albright, et al. (Document No. 129:54301) retrieved from STN; entered in STN on Jun. 17, 1998.
Lee, et al. (Document No. 140:69941) retrieved from STN; entered in STN on Jul. 8, 2003.
Zheng, et al. (Document No. 161:399872) retrieved from STN; entered in STN on Jul. 23, 2014.
Wang, et al. (Document No. 160:385666) retrieved from STN; entered in STN on Feb. 27, 2014.
Xiong, et al. (Document No. 160:101182) retrieved from STN; entered in STN on Nov. 12, 2013.
Heeney, et al. (Document No. 153:359062) retrieved from STN; entered in STN on Sep. 2, 2010.
Andrzej, et al. (Document No. 144:274313) retrieved from STN; entered in STN on Mar. 3, 2006.
Pubchem-CID: 10595203, p. 3, Fig, Oct. 25, 2006, 1-9.

PROCESSES FOR THE PREPARATION OF BENZODIAZEPINE DERIVATIVES

RELATED APPLICATIONS

This application claims the benefit of U.S. Provisional Application No. 62/459,955 filed on Feb. 16, 2017, and U.S. Provisional Application No. 62/459,953 filed on Feb. 16, 2017. The entire teachings of the above application are incorporated herein by reference.

TECHNICAL FIELD

The present invention relates to processes and intermediates useful in the preparation of biologically active molecules, especially in the synthesis of Respiratory Syncytial Virus (RSV) inhibitors.

BACKGROUND OF THE INVENTION

Human respiratory syncytial virus (HRSV) is a negative-sense, single stranded, RNA paramyxovirus (K M. Empey, et al., *Rev. Anti-Infective Agents,* 2010, 50 (1 May), 1258-1267). RSV is the leading cause of acute lower respiratory tract infections (ALRI) and affects patients of all ages. The symptoms in adults are usually not severe and are typically analogous to a mild cold. However, in infants and toddlers the virus can cause lower respiratory tract infections including bronchiolitis or pneumonia with many of them requiring hospitalization. Nearly all children have been infected by age 3. There are known high-risk groups that infection with RSV is more likely to progress into the ALRI. Premature infants and/or infants suffering from lung or cardiac disease are at the highest risk to develop ALRI. Additional high-risk groups include the elderly, adults with chronic heart and/or lung disease, stem cell transplant patients and the immunosuppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of palivizumab treatment limits its use for general purposes. Ribavirin has also been used to treat HRSV infections, but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO2013/186332, WO2012/080451, WO2012/080450, WO2012/080449, WO2012/080447, WO2012/080446, and *J. Med. Chem.* 2015, 58, 1630-1643. Examples of other N-protein inhibitors for treatment of HRSV have been disclosed in the following publications: WO2004/026843, *J. Med. Chem.* 2006, 49, 2311-2319, and *J. Med. Chem.* 2007, 50, 1685-1692. Examples of L-protein inhibitors for HRSV have been disclosed in the following publications: WO2011/005842, WO2005/042530, *Antiviral Res.* 2005, 65, 125-131, and *Bioorg. Med. Chem. Lett.* 2013, 23, 6789-6793. Examples of nucleosides/polymerase inhibitors have been disclosed in the following publications: WO2013/242525 and *J. Med. Chem.* 2015, 58, 1862-1878.

There is a need for the development of effective treatments for HRSV. The present invention has identified compounds that are aminoheteroaryl substituted benzodiazepines, and inhibit HRSV. The invention includes methods to prepare the compounds as well as methods of using these compounds to treat disease.

SUMMARY OF THE INVENTION

The present invention provides methods for preparing compounds of formula (I), or a pharmaceutically acceptable salt thereof:

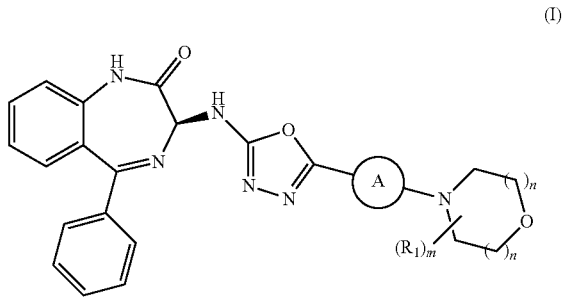

(I)

wherein Ⓐ is an optionally substituted aryl or optionally substituted heteroaryl, preferably Ⓐ is optionally substituted pyridyl; each n is independently selected from 1 and 2; preferably each n is 1; m is 0, 1, 2, 3, or 4; preferably m is 0;

$R_1$ is selected from the group consisting of:
1) optionally substituted —$C_1$-$C_8$ alkyl;
2) optionally substituted —$C_3$-$C_8$ cycloalkyl; and
3) optionally substituted 3- to 12-membered heterocyclic;

Alternatively, two adjacent $R_1$ groups are taken together with the carbon atoms to which they are attached to form a fused ring; two geminal $R_1$ groups are taken together with the carbon atom to which they are attached to form a spiro ring; or two $R_1$ groups on nonadjacent carbon atoms are taken together to form a bridging group, such as —$CH_2$— or —$CH_2CH_2$—.

Preferably, when m is not 0, each $R_1$ is methyl.

A preferred compound of formula (I) is compound (I-a):

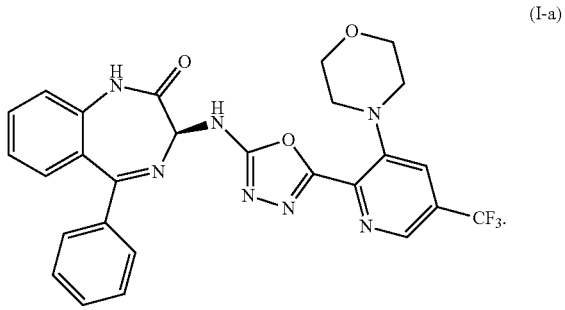 [SMILES: O=C1Nc2ccccc2C(c2ccccc2)=N[C@@H]1Nc1nnc(-c2ncc(C(F)(F)F)cc2N2CCOCC2)o1]

(I-a)

The invention further relates to methods for increasing product yield and decreasing process steps for intermediate and large scale production of compounds of formula (I), such as compound (I-a). These compounds are useful as RSV inhibitors.

DETAILED DESCRIPTION OF THE INVENTION

In its principal embodiment, the present invention provides a process for the preparation of a compound of formula (I), or a pharmaceutically acceptable salt thereof:

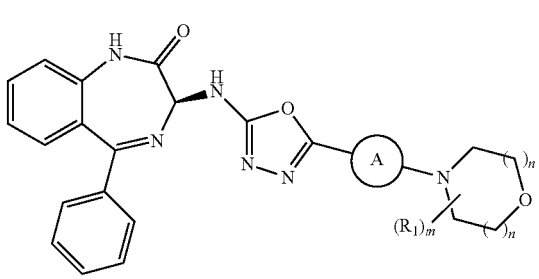
(I)

wherein Ⓐ, $R_1$, m and n are previously defined. In certain embodiments,

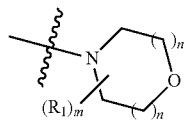

is selected from the groups set forth below:

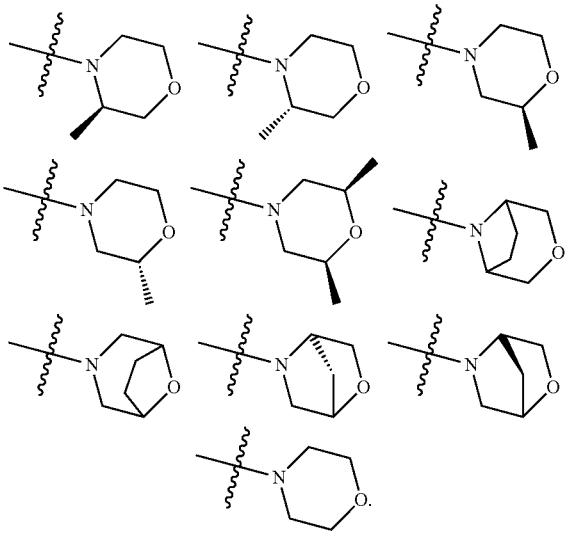

The process comprises the steps of
1) reacting a compound of formula (VII),

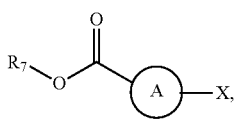
(VII)

wherein $R_7$ is selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, 3- to 8-membered heterocyclic, aryl, and heteroaryl; and X is a leaving group, such as, but not limited to, halogen or —O-triflate; with a compound of formula (VII-X),

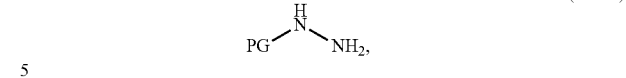
(VII-X)

wherein PG is hydrogen or an amine protecting group, such as, but not limited to cbz, Boc, methoxycarbonyl, or 9-fluorenyl-methoxycarbonyl;
to produce a compound of formula (VIII),

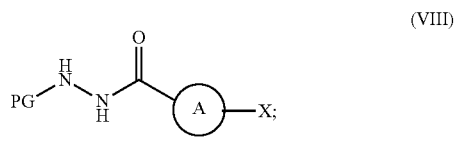
(VIII)

2) reacting the compound of formula (VIII) with a compound of formula (IX):

(IX)

wherein $R_1$, m and n are as previously defined; to produce a compound of formula (X):

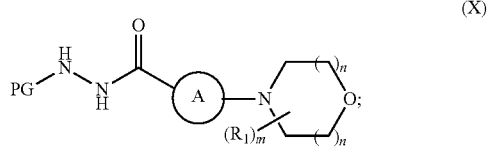
(X)

3) reacting the compound of formula (X) with a compound of formula (III),

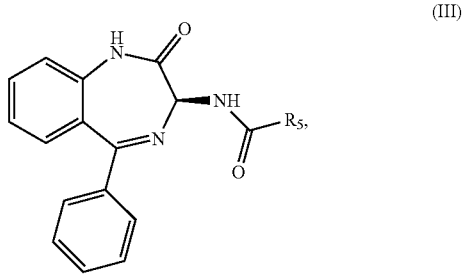
(III)

wherein $R_5$ is selected from the group consisting of —O(CO)O—$R_6$, optionally substituted aryl, and optionally substituted heteroaryl; and $R_6$ is selected from the group consisting of optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkenyl, optionally substituted 3- to 8-membered heterocyclic, optionally substituted aryl, and optionally substituted heteroaryl;

to form a compound of formula (V),

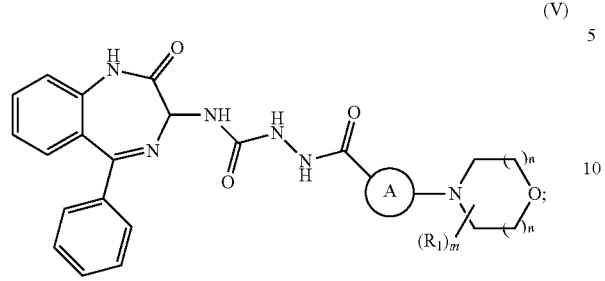
(V)

and 4) reacting the compound of formula (V) with a cyclizing reagent to form the compound of formula (I).

A preferred embodiment of a compound of formula (VIII) is a compound of formula (VIII-a), formula (VIII-b), or formula (VIII-c):

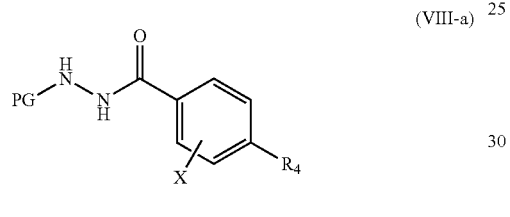
(VIII-a)

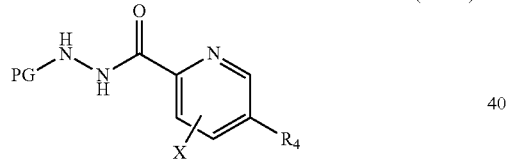
(VIII-b)

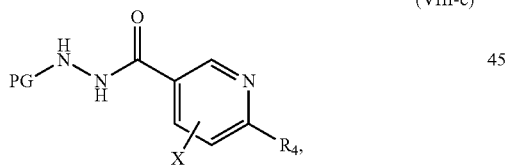
(VIII-c)

wherein $R_4$ is selected from halogen, methyl, $CF_3$, and CN.

A more preferred embodiment of a compound of formula (VIII) is a compound of formula (VIII-d),

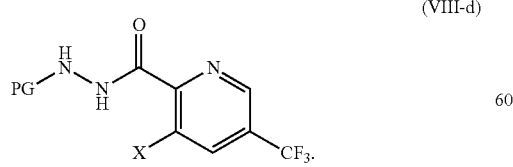
(VIII-d)

A preferred embodiment of a compound of formula (X) is a compound of formula (X-a), formula (X-b), or formula (X-c):

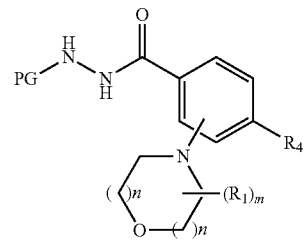
(X-a)

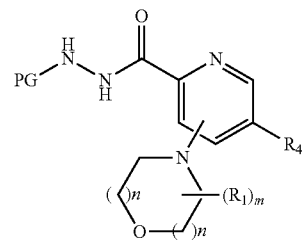
(X-b)

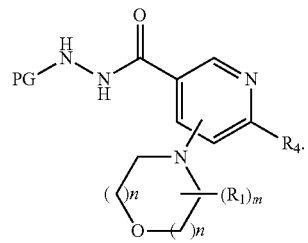
(X-c)

A more preferred embodiment of a compound of formula (X) is a compound of formula (X-d):

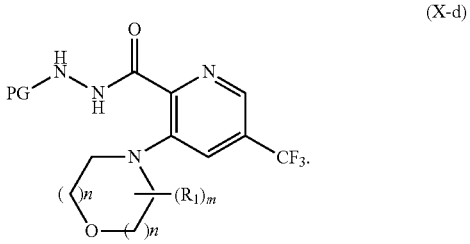
(X-d)

In a preferred embodiment, the compound of formula (III) is compound (III-a):

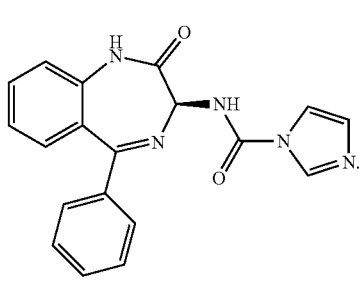
(III-a)

A preferred embodiment of the compound of formula (V) is compound (V-a).

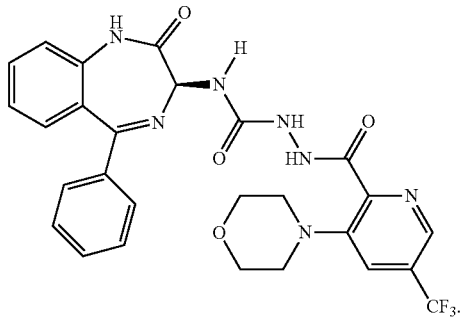

The compound of formula (III) can be formed by reacting compound (IV),

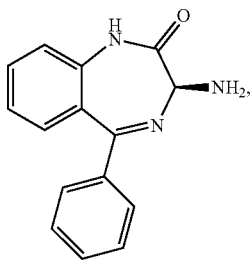

with an activating agent of the formula Y—C(O)R$_5$, wherein Y is a leaving group, such as halide or 1-imidazolyl.

Compound (IV) can be prepared, for example, by resolution of a racemic mixture of compound (IV) and its enantiomer.

In one embodiment, the invention provides a compound of formula (I), or a pharmaceutically acceptable salt thereof, in an amorphous solid form. In this embodiment, the compound of Formula I is preferably compound (I-a) or a pharmaceutically acceptable salt thereof and more preferably, the compound of formula (I) is compound (I-a) free base.

In another embodiment, the invention provides compositions comprising an amorphous solid form of a compound of formula (I) or a pharmaceutically acceptable salt thereof and a pharmaceutically acceptable hydrophilic polymer to enhance activity.

In one embodiment of this aspect of the invention, the hydrophilic polymer is selected from homopolymer of N-vinyl lactam, copolymers of N-vinyl lactam, cellulose esters, cellulose ethers, polyalkylene oxide, polyacrylate, polymethacrylate, polyacrylamide, polyvinyl alcohol, vinyl acetate polymer, oligosaccharides, and polysaccharides. Non-limiting examples of suitable hydrophilic polymers include homopolymer of N-vinyl pyrrolidone, copolymers of N-vinyl pyrrolidone, copolymers of N-vinyl pyrrolidone and vinyl acetate, copolymers of N-vinyl pyrrolidone and vinyl propionate, polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, or xanthan gum.

In yet another embodiment of this aspect of the invention, the hydrophilic polymer is a homopolymer or copolymer of N-vinyl pyrrolidone. Preferably, the hydrophilic polymer is copovidone.

The compositions comprising a compound of formula (I), or a pharmaceutically acceptable salt in an amorphous solid form and a pharmaceutically acceptable hydrophilic polymer can be prepared by a variety of techniques such as, without limitation, melt-extrusion, spray-drying, coprecipitation, freeze drying, or other solvent evaporation techniques, with melt-extrusion and spray-drying being preferred. The melt-extrusion process typically comprises the steps of preparing a melt which includes the active ingredient(s), the hydrophilic polymer(s) and preferably a surfactant(s), and then cooling the melt until it solidifies. "Melting" means a transition into a liquid or rubbery state in which it is possible for one component to become embedded, preferably homogeneously embedded, in the other component or components. In many cases, the polymer component(s) will melt and the other components including the active ingredient(s) will dissolve in the melt thereby forming a solution. Melting usually involves heating above the softening point of the polymer(s). The preparation of the melt can take place in a variety of ways. The mixing of the components can take place before, during or after the formation of the melt. For example, the components can be mixed first and then melted or be simultaneously mixed and melted. The melt can also be homogenized in order to disperse the active ingredient(s) efficiently. In addition, it may be convenient first to melt the polymer(s) and then to mix in and homogenize the active ingredient(s). In one example, all materials except surfactant(s) are blended and fed into an extruder, while the surfactant(s) is molten externally and pumped in during extrusion.

Synthetic Schemes

The present invention will be better understood in connection with schemes 1-2, wherein Ⓐ, R$_1$, PG, X, m, n, and R$_5$ are as previously defined unless otherwise indicated.

It will be readily apparent to one of ordinary skill in the art that the process of the present invention can be practiced by substitution of the appropriate reactants and that the order of the steps themselves can be varied.

A chemical route to the synthesis of the hydrazide, the compound of formula (X) is summarized in scheme 1.

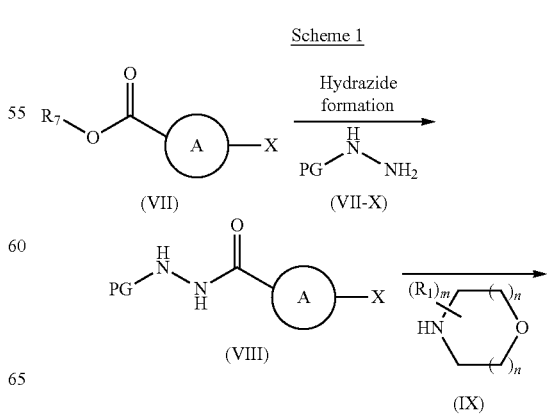

-continued

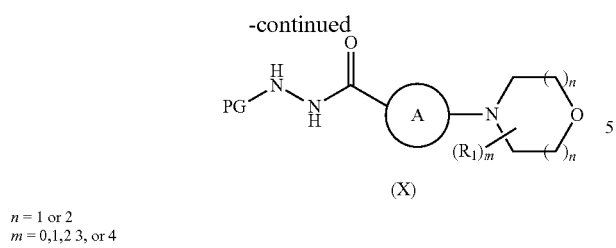

(X)

n = 1 or 2
m = 0,1,2 3, or 4

$R_7$ is selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, 3- to 8-membered heterocyclic, aryl, and heteroaryl. Preferably, the compound of formula (VII) is 3-halo-5-(trifluoromethyl)-2-pyridinecarboxylic acid or alkyl 3-halo-5-(trifluoromethyl) picolinate and more preferably ethyl 3-chloro-5-(trifluoromethyl)-picolinate, which is commercially available. Preferred compounds of formula (VII-X) include hydrazine monohydrate, Boc-hydrazine or Cbz-hydrazine.

In one embodiment, $R_7$ is $C_1$-$C_8$ alkyl, preferably methyl or ethyl. In this embodiment, the reaction of the compound of formula (VII) and hydrazine monohydrate typically takes place in a protic solvent such as, but not limited to, methanol, ethanol, or isopropyl alcohol or a mixture of two or more thereof. The reaction temperature is typically about 10° C. to about 70° C. and the reaction time is typically about 3 to 12 hours.

In another embodiment, $R_7$ is hydrogen, and the compound of formula (VII) is converted to the compound of formula (VIII) by coupling with a compound of formula (VII-X) in the presence of an amide coupling agent such as 1,1'-carbonyldiimidazole, bis(2-oxo-3-oxazolidinyl)-phosphinic chloride, 1-hydroxy-7-azabenzotriazole, 1-hydroxybenzotriazole hydrate, 3-hydroxy-1,2,3-benzotriazin-4(3H)-one, 1-(3-dimethyaminopropyl)-3-ethylcarbodiimide hydrochloride, 4-nitrophenol, pentafluorophenol, 2-hydroxypyridine, N-hydroxysuccinimide, N-hydroxyphthalamide, 2-mercaptobenzoxazole, trimethylacetyl chloride, isobutylchloroformate, chlorodimethoxytriazole, oxalyl chloride, 2-hydroxypyridine-N-oxide, 5-nitro-2-hydroxypyridine, Boc-L-valine anhydride, or mixtures thereof. Examples of suitable solvents for this reaction include, but are not limited to, isopropyl acetate, ethyl acetate, dichloromethane, acetone, THF, NMP, 2-methyltetrahydrofuran, and acetonitrile. Particular reaction conditions will vary depending on the nature of the coupling reagent and will be known to those of ordinary still in the art.

A compound of formula (VIII) can be transformed to a compound of formula (X) by amination with a compound of formula (IX), The compound of formula (IX) can be, but is not limited to, morpholine, 2-methylmorpholine and its stereoisomers, 3-methylmorpholine and its stereoisomers, 3,5-dimethylmorphine and its stereoisomers, 2,6-dimethylmorphine and its stereoisomers, 3-oxa-8-azabicyclo[3.2.1]octane, 2-oxa-5-azabicyclo[2.2.1]heptane, 8-oxa-3-azabicyclo[3.2.1]octane. The reaction typically takes place as neat or in an aprotic solvent, such as, but not limited to toluene, THF or dichloromethane. The reaction temperature is typically about 10° C. to about 100° C. and the reaction time is typically 3 to 12 hours.

In one embodiment, wherein PG is not hydrogen, the compound of formula (X) is deprotected by removing PG. Suitable deprotection conditions depend on the identity of PG and are known to those skilled in the art, for example, as described generally in T. H. Greene and P. G. M. Wuts, *Protective Groups in Organic Synthesis*, 3rd edition, John Wiley & Sons, New York (1999).

Scheme 2 illustrates the synthesis of the compound of formula (I),

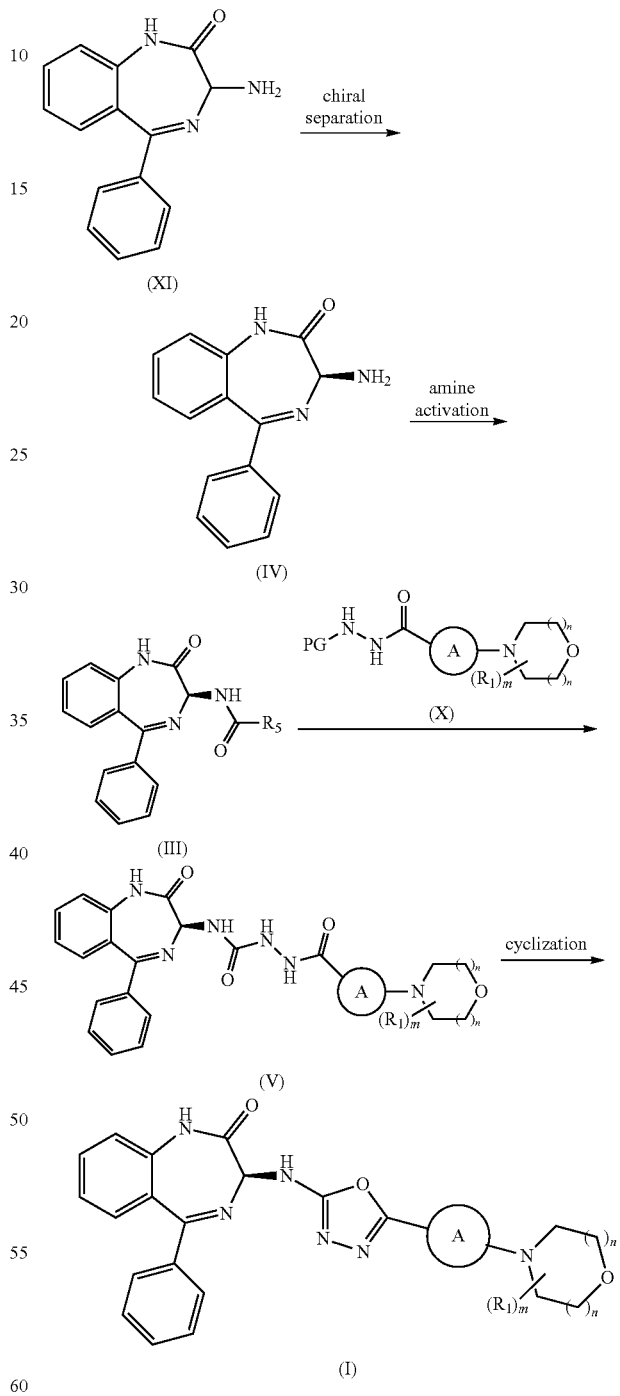

The compound (XI) is either commercially available or can be synthesized by methods known to those of ordinary skill in the art. The chiral separation of the racemic compound (XI) can be performed using methods such as, but not limited to, treatment with a chiral acid and separation of the diastereoisomeric salt by crystallization or chromatography, capillary electrophoresis (CE), supercritical fluid chromatography (SFC), capillary electrochromatography (CEC), gas chromatography (GC), high performance liquid chromatography (HPLC), and crystallization with chiral salts, then following separation of diasteromeric analogs to provide a chiral compound (IV), S-isomer. In one embodiment, compound (IV) is produced from racemic compound (XI) using the method disclosed in U.S. Provisional Application No. 62/585,192.

In one embodiment, SFC is used to obtain chiral compound (IV), the mobile phase is carbon dioxide ($CO_2$) or a mixture of carbon dioxide and a polar organic co-solvent such as, but not limited to, methanol, ethanol, or 2-propanol; the temperature range is limited from 5 to 40-50° C., preferably, the temperature is room temperature (about 25° C.). The procedures and conditions of SFC will vary and depend on the nature of racemic compounds and will be known to those ordinary skills in the art.

In one aspect, chiral compound (IV) is obtained with greater than about 90% enantiomeric excess purity (ee) after SFC separation. In one aspect, chiral compound (IV) is obtained with greater than about 95% enantiomeric excess purity (ee) after SFC separation. In one aspect, chiral compound (IV) is obtained with greater than about 98% enantiomeric excess purity (ee) after SFC separation.

In one embodiment, after chiral separation, besides chiral compound (IV), another epimer, chiral compound (IV-A), R-isomer, is also obtained:

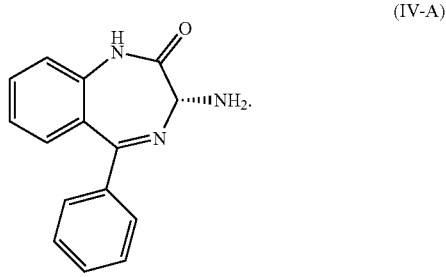 [SMILES: N[C@@H]1N=C(c2ccccc2)c2ccccc2NC1=O]

(IV-A)

In one embodiment, the chiral compound (IV-A), is racemized under basic conditions to obtain racemic compound (XI). The racemization takes place in a protic solvent, such as, but not limited to, methanol, ethanol, $^t$BuOH or isopropyl alcohol, in the presence of a base, such as, but not limited to NaOMe or $^t$BuOK. The reaction temperature is typically about 10° C. to about 70° C. and the reaction time is typically about 3 to 24 hours.

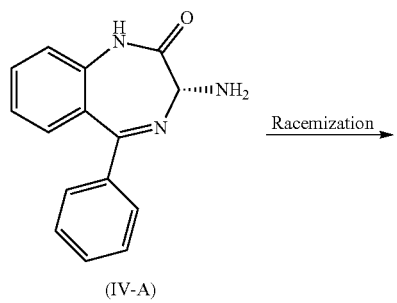

(IV-A)

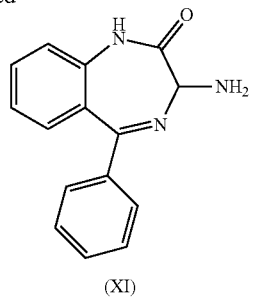

(XI)

In one embodiment, the chiral compound (IV) is transformed to a compound of formula (III) by reaction with an amine activation agent, such as, but not limited to, 1,1'-carbonyldiimidazole, nitrophenyl chloroformate, triphosgene or phosgene. This process is typically carried out in a protic or aprotic solvent such as, but not limited to, acetonitrile, THF, DMSO, or dichloromethane. The typical reaction temperature is about 0° C. to 30° C. and the reaction time is typically about 6 to 15 hours. In one aspect, the molar ratio of compound (IV) and amine activation agent is about 1 to 1. In one aspect, the molar ratio of compound (IV) and the amine activation agent is about 1 to 2. In one aspect, the molar ratio of the chiral compound (IV) and the amine activation agent is about 1 to 3. Preferably, the molar ratio of the chiral compound (IV) and the amine activation agent is about 1 to 3.

In one embodiment, PG is hydrogen, the reaction of the compound of formula (III) with the compound of formula (X) is carried out in a protic solvent such as, but not limited to, acetonitrile, THF, DMSO, DMF, sulfolane or 1-methyl-2-pyrrolidone. The typical reaction temperature is about 10 to 50° C. and the reaction time is typically 6 to 48 hours. The reaction is typically conducted at a concentration of the compound of formula (III) about 1 M to 3 M, preferably the concentration of the compound of formula (III) is 1.5M. The molar ratio of the compound of formula (III) and the compound of formula (X) is 1:1.

The compound of formula (V) can be cyclized to a compound of formula (I) by reaction with a cyclizing agent, such as, but not limited to, p-toluenesulfonyl chloride, thionyl chloride, phosphorous oxychloride or HATU in the presence of an organic base. Suitable organic bases include, but are not limited to, triethylamine and diisopropylethylamine. This process is carried out in an aprotic solvent, such as, but not limited to, acetonitrile, THF, DMF, DMSO, NMP, acetone, dichloromethane, ethyl acetate or isopropyl acetate. The reaction temperature is about 0° C. to about 30° C., and the reaction time is typically 3 to 15 hours.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with an exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH— heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)— heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$— $C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$— $C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, cycloalkyls and the like can be further substituted.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus, a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethyl succinates.

Suitable concentrations of reactants used in the synthesis processes of the invention are 0.01M to 10M, typically 0.1M to 1M. Suitable temperatures include −10° C. to 250° C., typically −78° C. to 150° C., more typically −78° C. to 100° C., still more typically 0° C. to 100° C. Reaction vessels are preferably made of any material which does not substantial interfere with the reaction. Examples include glass, plastic, and metal. The pressure of the reaction can advantageously be operated at atmospheric pressure. The atmospheres include, for example, air, for oxygen and water insensitive reactions, or nitrogen or argon, for oxygen or water sensitive reactions.

The term "in situ," as used herein, refers to use of an intermediate in the solvent or solvents in which the intermediate was prepared without removal of the solvent.

Abbreviations

Abbreviations which may be used in the descriptions of the scheme and the examples that follow are:

Ac for acetyl;
AcOH for acetic acid;
$Boc_2O$ for di-tert-butyl-dicarbonate;
Book for t-butoxycarbonyl;
BSc for benzoyl;
Bn for benzyl;
Brine for sodium chloride solution in water;
t-BuOH for tert-butanol;
t-BuOK for potassium tert-butoxide;
$Bu_4NBr$ for tetrabutylammonium bromide;
Cob for carbobenzyloxy;
CDI for 1,1'-carbonyldiimidazole;
$CH_2C_{12}$ for dichloromethane;
$CH_3$ for methyl;
$CH_3CN$ for acetonitrile;
$Cs_2CO_3$ for cesium carbonate;
DIBAL-H for diisobutylaluminium hydride;
DIPEA or $(i-Pr)_2EtN$ for N,N-diisopropylethylamine;
DMAP for 4-dimethylamino-pyridine;
DME for 1,2-dimethoxyethane;
DMF for N,N-dimethylformamide;
DMSO for dimethyl sulfoxide;
EDC for N-(3-dimethylaminopropyl)-N'-ethylcarbodiimide;
EDC.HCl for N-(3-dimethylamino-propyl)-N'-ethylcarbodiimide hydrochloride; EtOAc for ethyl acetate;
EtOH for ethanol;
$Et_2O$ for diethyl ether;
HATU for O-(7-azabenzotriazol-1-yl)-N,N,N',N'-tetramethyluronium hexafluorophosphate;
HCl for hydrogen chloride;
$K_2CO_3$ for potassium carbonate;
MeOH for methanol;
MTBE for methyl tert-butyl ether;
NaCl for sodium chloride;
NaH for sodium hydride;
$NaHCO_3$ for sodium bicarbonate or sodium hydrogen carbonate;
$Na_2CO_3$ sodium carbonate;
NaOH for sodium hydroxide;
NaOMe for sodium methoxide;
$Na_2SO_4$ for sodium sulfate;
$Na_2S_2O_3$ for sodium thiosulfate;
$NH_4HCO_3$ for ammonium bicarbonate;
$NH_4Cl$ for ammonium chloride;
NMP for N-Methyl-2-pyrrolidone o/n for overnight;
OH for hydroxyl;
Pd for palladium;
PDC for pyridinium dichromate;
i-PrOAc for isopropyl acetate;
Ph for phenyl;
PMB for p-methoxybenzyl;
rt for room temperature;
TBS for tert-butyl dimethylsilyl;
TEA or $Et_3N$ for triethylamine;
THF for tetrahydrofuran;
TPP or $PPh_3$ for triphenylphosphine;
Ts for tosyl or —$SO_2$—$C_6H_4CH_3$;

TsOH for p-tolylsulfonic acid;
TMS for trimethylsilyl;
TMSCl for trimethylsilyl chloride.

All other abbreviations used herein, which are not specifically delineated above, shall be accorded the meaning which one of ordinary skill in the art would attach.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of 3-morpholino-5-(trifluoromethyl)picolinohydrazide

Step 1. Synthesis of 3-Chloro-5-(trifluoromethyl)picolinohydrazide

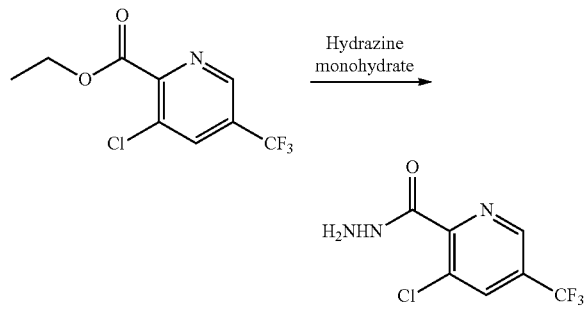

Into a 50-L 4-necked round-bottom flask purged and maintained with an inert atmosphere of nitrogen, was placed a solution of ethyl 3-chloro-5-(trifluoromethyl)pyridine-2-carboxylate (4.0 kg, 15.81 mol, 1.00 equiv) in ethanol (12 L) and treated with hydrazine monohydrate (1.98 kg, 2.00 equiv). The resulting solution was stirred for 2 h at 20° C. in a water bath. The resulting solution was quenched to 24 L of ice water, stirred for 30 min. The solids were filtered out. The resulting solution was extracted with 7×8.5 L of MTBE (7×8.8 L) and the organic layers combined, dried over sodium sulfate, filtered and concentrated under vacuum to afford the title compound (3.65 kg) as a yellow solid. LC-MS(ESI, m/z): 240.0 [M+H]$^+$.

Step 2. Synthesis of 3-morpholino-5-(trifluoromethyl)picolinohydrazide

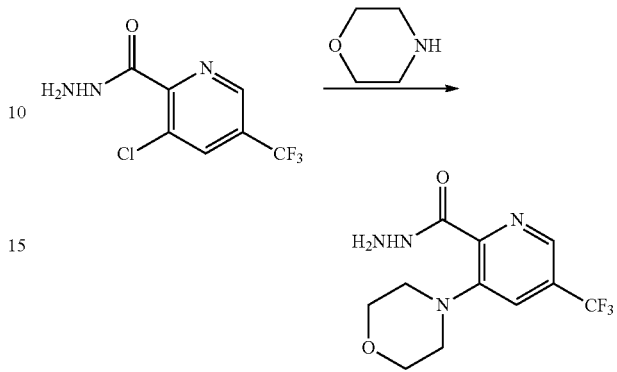

Into a 50-L 4-necked round-bottom flask purged and maintained with an inert atmosphere of nitrogen, was placed a solution of 3-chloro-5-(trifluoromethyl)pyridine-2-carbohydrazide (3.5 kg, 14.61 mol, 1.00 equiv) in toluene (17.5 L), morpholine (6.38 kg, 73.22 mol, 5.00 equiv). The resulting solution was stirred for 18 h at 96° C. in an oil bath. The reaction mixture was cooled to 25° C. with a water bath. The solid was collected by filtration. The resulting mixture was concentrated under vacuum. The combined solid was washed with tetrahydrofuran (9×4.5 L). The solid was filtered out. The filtrate was concentrated under vacuum. The residue was slurried with MTBE (10 L) and stirred for 2 hrs. The solid collected by filtration. This reaction was repeated with another amount of 3 kg of SM under the same conditions and the same procedure. The crude of two batches was combined, washed with MTBE (4 L) and dried under vacuum to give the title compound (6.1 kg) as a light yellow solid. LC-MS (ES, m/z): 291.0 [MS+H$^+$]. $^1$H-NMR (300 MHz, DMSO-d$_6$): δ 9.63 (s, 1H), 8.49 (s, 1H), 7.71 (s, 1H), 4.54 (m, 2H), 3.77-3.68 (m, 4H), 3.18-3.06 (m, 4H).

Example 2

Preparation of (S)-3-((5-(3-morpholino-5-(trifluoromethyl)pyridin-2-yl)-1,3,4-oxadiazol-2-yl)amino-5-phenyl-1,3-dihydro-2H-benzo[e] [1,4]-diazepin-2-one (Compound (I-a))

Step 1: SFC Chiral Separation of 3-Amino-5-phenyl-1,3-dihydro-2H benzo[e] [1,4]-diazepin-2-one

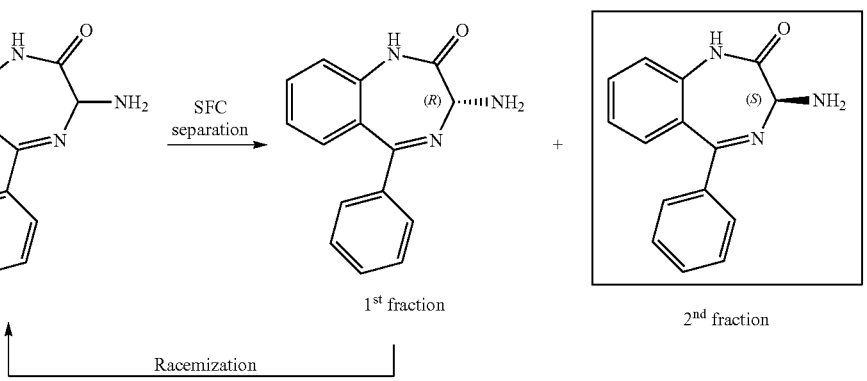

3-Amino-5-phenyl-1,3-dihydro-2H-benzo[e] [1,4]-diazepin-2-one (13.0 kg) was separated by SFC [Instrument: Waters 200 preparative SFC], Column: Chiral Pak AD, 250×50 mm I.D., 10 μm. Mobile phase: A fo r $CO_2$ and B for 2-propanol (0.1% $NH_3H_2O$), Gradient: B 45% Flow rate: 180 mL/min]. The first fraction ((R)-3-amino-5-phenyl-1,3-dihydro-2H-benzo[e] [1,4]-diazepin-2-one, 5.0 kg, 38.5% yield) was collected as a light yellow solid. The second fraction ((S)-3-amino-5-phenyl-1,3-dihydro-2H-benzo[e] [1,4]-diazepin-2-one, was concentrated under reduced pressure, dried under high vacuum to afford the title compound (5.13 kg, 39.5% yield) as a light yellow solid. $^1$H NMR: (DMSO-$d_6$ 400 MHz): δ 10.68 (br, 1H), 7.60-7.56 (m, 1H), 7.48-7.40 (m, 5H), 7.27-7.24 (m, 2H), 7.21-7.17 (m, 1H), 4.24 (s, 1H). HPLC purity: 100%; Chiral purity: 99.94% ee. LC-MS(ESI, m/z): 252.0 $[M+H]^+$.

Step 2: Racemization of (R)-3-Amino-5-phenyl-1,3-dihydro-2H benzo[e] [1,4]-diazepin-2-one to 3-amino-5-phenyl-1,3-dihydro-2H benzo[e] [1,4]-diazepin-2-one

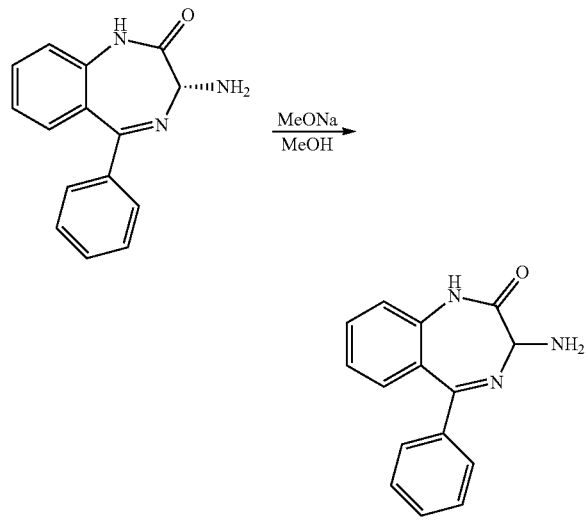

The first fraction ((R)-3-amino-5-phenyl-1,3-dihydro-2H-benzo[e] [1,4]-diazepin-2-one) was racemized and used for SFC separation as following: (R)-3-amino-5-phenyl-1,3-dihydro-2H-benzo[e] [1,4]-diazepin-2-one (1.0 kg) in MeOH (10 L) was treated with NaOMe (171 g) and heated at 60° C. for 16 hrs. After cooled to 25° C., the resulting mixture was quenched by addition ice-water (10 L) at 25° C. and concentrated under pressure to remove most of MeOH giving a precipitate. The residue was triturated with additional 5 L water and filtrated and dried under vacuum to afford racemic 3-amino-5-phenyl-1,3-dihydro-2H benzo[e] [1,4]-diazepin-2-one (0.9 kg) as a pale yellow solid. $^1$H NMR: (DMSO-$d_6$ 400 MHz): δ 10.66 (br, 1H), 7.58-7.54 (m, 1H), 7.46-7.38 (m, 5H), 7.25-7.22 (m, 2H), 7.19-7.15 (m, 1H), 4.22 (s, 1H). HPLC Purity: 99.7%; LC-MS(ESI, m/z): 252.2 $[M+H]^+$.

The racemic amine obtained above was separated again by using preparative SFC.

Step 3. Preparation of (S)—N-(2-oxo-5-phenyl-2,3-dihydro-1H-benzo[e][1,4]-diazepin-3-yl)-1H-imidazole-1-carboxamide

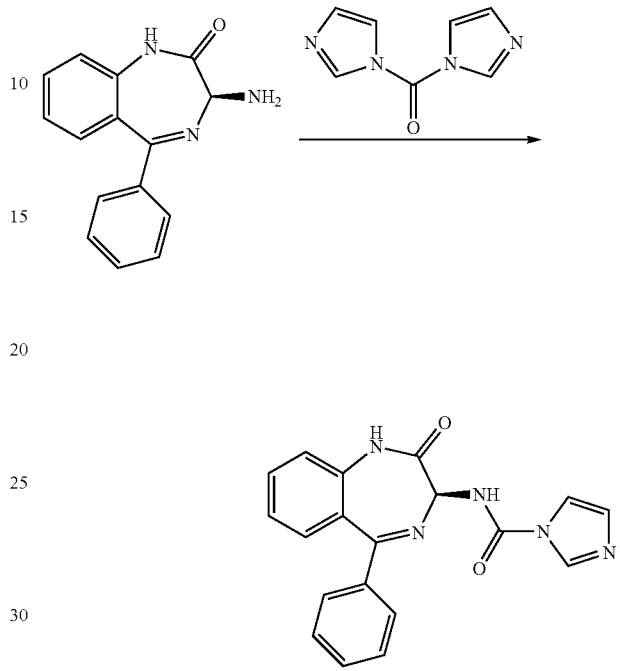

1,1'-carbonyldiimidazole (1.65 kg, 3.0 eq.) was added in a reactor filled with MeCN (12.7 L) at 20±5° C., stirred for 15 min and cooled to 0±3° C. (S)-3-amino-5-phenyl-1,3-dihydro-2H-benzo[e] [1,4]-diazepin-2-one (0.85 kg, 1.0 eq.) in batches maintaining below 5° C. during addition. The reaction was stirred at 2±3° C. for 2 hrs. and warmed to 20±5° C. and stirred for 6 hrs. Then, the reaction was cooled to 0±3° C., treated with purified water (365.5 g, 6.0 eq.) in MeCN solution (4.25 L) below 8° C. within 1.5 h and warmed to 20° C. The solid was filtered and washed with (1.7 L, 2 V) twice. The collected solid was dried in vacuum oven at <25° C. to afford the title compound (1.16 kg, 98.6% purity by HPLC) as a white solid. LC-MS(ESI, m/z): 278.10, 346.13 $[M+H]^+$.

Step 4: (S)-2-(3-morpholino-5-(trifluoromethyl) picolinoyl)-N-2-oxo-5-phenyl-2,3-dihydro-1H-benzo [e][1,4]diazepin-3-yl)hydrazine-1-carboxamide

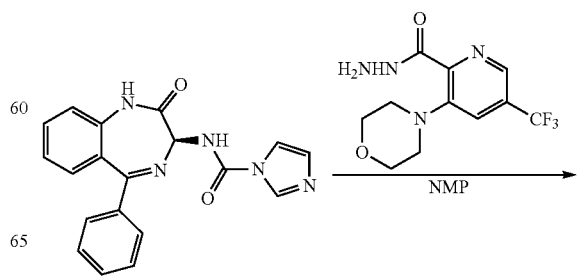

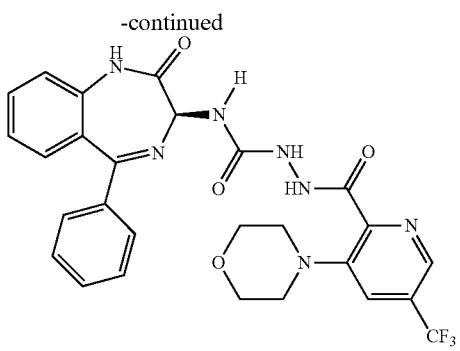

3-Morpholino-5-(trifluoromethyl)picolinohydrazide (0.84 kg, 1.0 eq.) was added into 5 L-flask filled with NMP (2 L) at 25±5° C. and stirred for 10 min.

(S)—N-(2-oxo-5-phenyl-2,3-dihydro-1H-benzo[e][1,4]-diazepin-3-yl)-1H-imidazole-1-carboxamide (1.0 kg, 1.0 eq.) was added to the reaction in batches at 25±5° C. and heated at 45° C. for 10 hrs. The reaction mixture was cooled to 15° C., poured into ice-water (15 L, 3° C.) in 20 L flask, stirred for 30 min, filtered and washed with purified water (2×3 L). The collected cake was stirred with purified water (10 L) at 25±5° C. for 1 hr, filtered and washed with purified water (2×3 L). The collected cake was dried under vacuum oven at 27° C. for 40 h to give the crude (1.640 kg). The crude (1.64 kg) was dissolved in DCM (10 L), stirred for 30 min, charged with active carbon (0.15 kg) and stirred for 30 min, filtered through diatomite (1 wt/wt), washed with DCM (2×2.5 L). The filtrate was charged with n-heptane (30 L) in 50L round-bottomed flask at 25±5° C. and stirred for 1 hr. The solid was filtered and wash the cake with n-heptane (2×2 L), dried under vacuum oven at 27° C. for 30 hrs to give the title compound (1.43 kg, 95.3% purity by HPLC) as a light-yellow solid. LC-MS(ESI, m/z): 568.19 [M+H]$^+$.

Step 5: (S)-3-((5-(3-morpholino-5-(trifluoromethyl)pyridin-2-yl)-1,3,4-oxadiazol-2-yl)amino-5-phenyl-1,3-dihydro-2H-benzo[e] [1,4]-diazepin-2-one

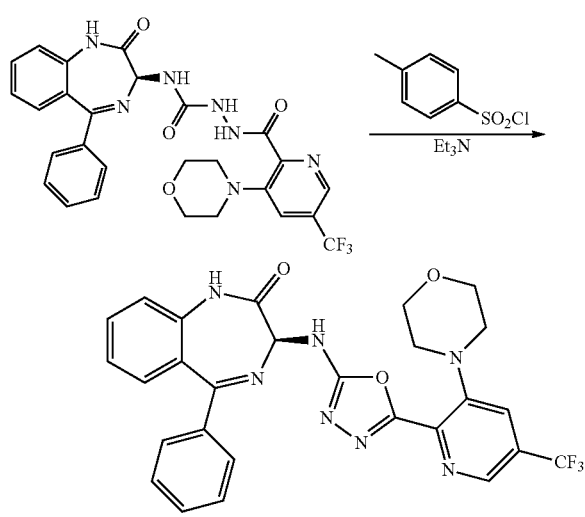

To a mixture of (S)-2-(3-morpholino-5-(trifluoromethyl)picolinoyl)-N-2-oxo-5-phenyl-2,3-dihydro-1H-benzo[e][1,4]diazepin-3-yl)hydrazine-1-carboxamide (1.4 kg, 1 eq.) in DCM (11.2 L) in a flask was charged with 4 Å-MS (1.4 kg) and stirred at 20±5° C. for 2 hrs. Then, it was cooled to 0° C., charged with triethylamine (0.62 Kg, 2.5 eq.) and stirred for 10 min. p-Toluenesulfonyl chloride (0.7 kg, 1.5 eq.) in DCM (1.4 L) solution was dropwise added to the reaction mixture with maintaining below 5° C. and stirred at 0±5° C. for 5 hrs. The reaction mixture was filtered and washed with DCM (2×4.2 L). The filtrate was treated with water (4.2 L) at 0° C. and stirred between 0 and 10° C. for 5 min. After separation, the organic phase was washed with 5% aqueous NaHCO$_3$ solution (7 L), water (7 L) and brine (7 L) successively and separated. The DCM layer was concentrated in vacuo at below 30° C. to leave ~7 L of organic layer. MTBE (7 L) was added to organic layer and concentrated in vacuo to leave ~7 L of organic layer (This step was repeated once). The organic layer was charged with water (7 L) and stirred at 20±5° C. for 4 hrs. The solid was filtered and washed with MTBE (3×2.1 L) and purified water (2.8 L). The wet cake was stirred with ethyl acetate (7 L) for 12 hrs, charged with n-heptane (14 L) and stirred at 20±5° C. for 5 hrs. The solid was filtered, washed with n-heptane (2×2.8 L) and dried under vacuum at ambient temperature to provide the title compound (0.776 kg, 99.6% purity by HPLC, 97.8% chiral purity by chiral HPLC) as a pale yellowish solid. LC-MS(ESI, m/z): 550.17 [M+H]$^+$;

$^1$H NMR: (DMSO-d$_6$ 400 MHz): δ 10.98 (br-s, 1H), 9.40 (d, J=8.0 Hz, 1H), 8.69 (br-d, J=4.0 Hz, 1H), 7.89 (d, J=4.0 Hz, 1H), 7.68 (dt, J=8.0 and 4.0 Hz, 1H), 7.56~7.51 (m, 3H), 7.49~7.45 (m, 2H), 7.38~7.35 (m, 2H), 7.29 (br-t, J=8.0 Hz, 1H) 5.22 (d, J=8.0 Hz, 1H), 3.75~3.72 (m, 4H), 3.09~3.07 (m, 4H); $^{13}$C (DMSO-d$_6$, 100 MHz): δ 167.3, 167.0, 162.8, 156.4, 147.2, 139.2, 138.7, 138.4, 138.3, 138.0, 132.30, 130.7, 130.5, 129.5, 128.4, 126.2, 124.5, 123.4, 121.5, 71.8, 65.9, 51.0.

Example 3

Preparation of an amorphous form of (S)-3-((5-(3-morpholino-5-(trifluoromethyl)pyridin-2-yl)-1,3,4-oxadiazol-2-yl)amino-5-phenyl-1,3-dihydro-2H-benzo[e] [1,4]-diazepin-2-one (S)-3-((5-(3-morpholino-5-(trifluoromethyl)pyridin-2-yl)-1,3,4-oxadiazol-2-yl)amino-5-phenyl-1,3-dihydro-2H-benzo[e] [1,4]-diazepin-2-one (60.0 g) was dissolved in acetic acid (170 mL), stirred for 10 min, filtered through a fritted funnel into 3 L-flask and lyophilized. It was dried further on vacuum pump at room temperature for 3 days. It was ground in a mortar and dried on vacuum with N$_2$ flow for 3 days to provide an amorphous form of (S)-3-((5-(3-morpholino-5-(trifluoromethyl)pyridin-2-yl)-1,3,4-oxadiazol-2-yl)amino-5-phenyl-1,3-dihydro-2H-benzo[e] [1,4]-diazepin-2-one as a yellowish solid.

Example 4

Preparation of a complex of amorphous Compound (I-a) [(S)-3-((5-(3-morpholino-5-(trifluoromethyl)pyridin-2-yl)-1,3,4-oxadiazol-2-yl)amino-5-phenyl-1,3-dihydro-2H-benzo[e] [1,4]-diazepin-2-one] with copovidone A mixture of (S)-3-((5-(3-morpholino-5-(trifluoromethyl)pyridin-2-yl)-1,3,4-oxadiazol-2-yl)amino-5-phenyl-1,3-dihydro-2H-benzo[e] [1,4]-diazepin-2-one (6.4 g) and copovidone (poly(1-vinylpyrrolidone-co-vinyl acetate), 1.6 g) were dissolved in acetone (160 mL). The solution was concentrated in vacuo and further dried under high vacuum pump for 2 days. The resulting solid was ground with a mortar and pestle and further dried in a vacuum oven at 45° C. for overnight to afford an amorphous form of (S)-3-((5-(3-morpholino-5-(trifluoromethyl)pyridin-2-yl)-1,3,4-oxadiazol-2-yl)amino-5-phenyl-1,3-dihydro-2H-benzo[e] [1,4]-diazepin-2-one/copovidone complex as a yellowish solid.

While this invention has been particularly shown and described with references to preferred embodiments thereof, it will be understood by those skilled in the art that various changes in form and details may be made therein without departing from the scope of the invention encompassed by the appended claims.

What is claimed:

1. A process for preparing a compound of formula (I),

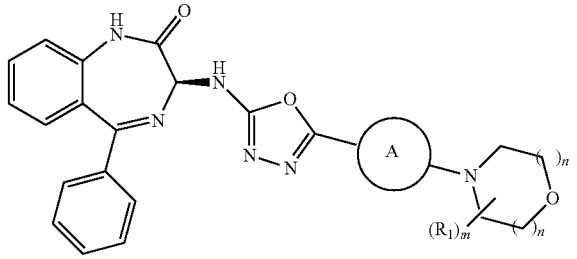
(I)

wherein

Ⓐ is an optionally substituted aryl or optionally substituted heteroaryl; each n is independently selected from 1 and 2;

m is 0, 1, 2, 3, or 4; and $R_1$ is selected from the group consisting of:
1) optionally substituted —$C_1$-$C_8$ alkyl;
2) optionally substituted —$C_3$-$C_8$ cycloalkyl;
3) optionally substituted 3- to 12- membered heterocyclic;

alternatively, two adjacent $R_1$ groups are taken together with the carbon atoms to which they are attached to form a fused ring; two geminal $R_1$ groups are taken together with the carbon atom to which they are attached to form a spiro ring; or two $R_1$ groups on nonadjacent carbon atoms are taken together to form a bridging group;

said process comprising the steps of:

(a) reacting a compound of formula (VII),

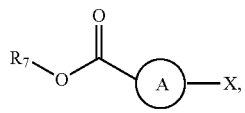
(VII)

wherein $R_7$ is selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, 3- to 8- membered heterocyclic, aryl, and heteroaryl; and X is a leaving group;

with a compound of formula (VII-X),

(VII-X)

wherein PG is hydrogen or an amine protecting group;

to produce a compound of formula (VIII):

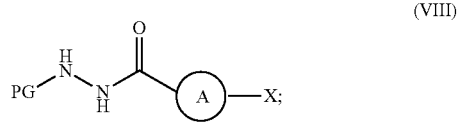
(VIII)

(b) reacting the compound of formula (VIII) with a compound of formula (IX):

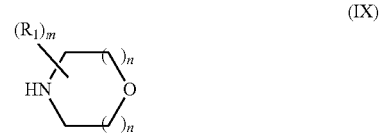
(IX)

to produce a compound of formula (X):

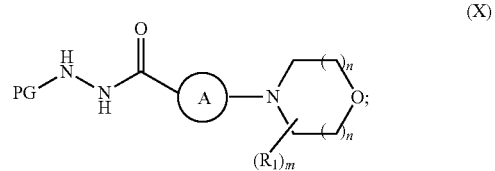
(X)

(c) reacting the compound of formula (X) with a compound of formula (III)

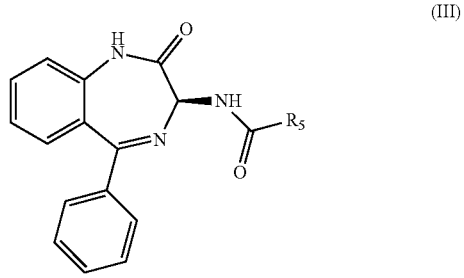
(III)

wherein $R_5$ is selected from the group consisting of —O(CO)O—$R_6$, optionally substituted aryl, and optionally substituted heteroaryl; and $R_6$ is selected from the group consisting of optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkenyl, optionally substituted 3- to 8 membered heterocyclic, optionally substituted aryl, and optionally substituted heteroaryl;

to produce a compound of formula (V),

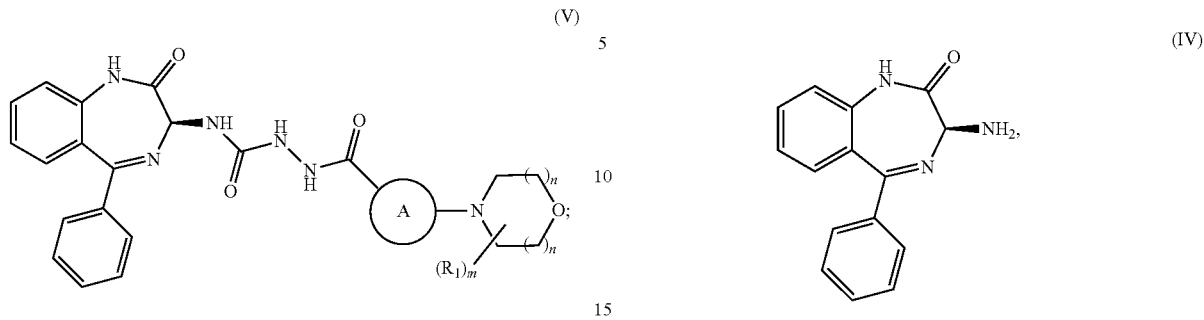

and (d) reacting the compound of formula (V) with a cyclizing reagent to form the compound of formula (I).

2. The process of claim 1, wherein

[structure] is [structure]

3. The process of claim 1, wherein step (a) is conducted in a protic solvent at a temperature of about 10° C. to about 70° C.

4. The process of claim 1, wherein $R_7$ is hydrogen, and step (a) is conducted in the presence of an amide coupling agent.

5. The process of claim 4, wherein the amide coupling agent is HATU or EDU.

6. The process of claim 4, wherein step (a) is conducted in a solvent selected from the group consisting of isopropyl acetate, ethyl acetate, dichloromethane, acetone, THF, NMP, 2-methyltetrahydrofuran, and acetonitrile.

7. The process of claim 1, wherein $R_7$ is $C_1$-$C_8$ alkyl, and step (a) is conducted in the presence of protic solvent.

8. The process of claim 7, wherein the protic solvent is methanol, ethanol, or isopropyl alcohol.

9. The process of claim 8, wherein step (a) is conducted at a temperature of about 10° C. to about 70° C. for about 3 to 12 hours.

10. The process of claim 1, wherein step (b) is conducted (i) neat or (ii) in an aprotic solvent; at a temperature about 10° C. to about 100° C.

11. The process of claim 1 further comprising the step of reacting compound (IV),

[structure (IV)]

with a compound of the formula Y—C(O)$R_5$, wherein Y is a leaving group, to produce the compound of formula (III).

12. The process of claim 11, wherein the compound of the formula Y—C(O)$R_5$ is 1,1'-carbonyldiimidazole or nitrophenyl chloroformate.

13. The process of claim 12, wherein the compound of formula IV is reacted with the amine activating agent is a solvent selected from the group consisting of acetonitrile, THF, DMSO, and dichloromethane.

14. The process of claim 1, wherein in step (c) is conducted in acetonitrile, THF, DMSO, DMF, sulfolane or 1-methyl-2-pyrrolidone.

15. The process of claim 14, wherein step (c) is conducted for 6 to 48 hours at a temperature of about 10 to 50° C.

16. The process of claim 1, wherein the cyclizing agent of step (d) is para-toluenesulfonyl chloride.

17. The process of claim 16, wherein step (d) is conducted (i) in the presence of triethylamine or diisopropylethylamine; (ii) in a solvent selected from the group consisting of acetonitrile, THF, DMF, DMSO, NMP, acetone, dichloromethane, ethyl acetate and isopropyl acetate; (iii) at a temperature from about 0° C. to about 30° C., (iv) for about 3 to 15 hours; (v) with a concentration of the compound of formula (III) of about 1 M to 3 M, and (vi) at a ratio of the concentration of the compound of formula (III) and the concentration of the compound of formula (V) of about 1:1.

18. The process of claim 1, wherein the compound of formula I is compound I-a:

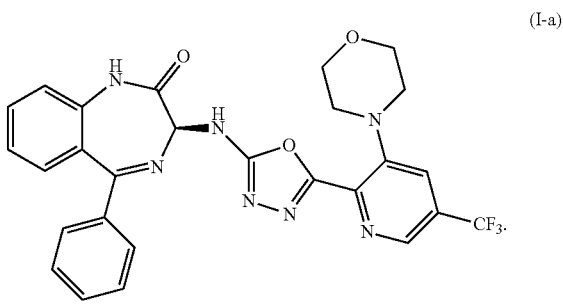 [SMILES: O=C1Nc2ccccc2C(c2ccccc2)=N[C@@H]1Nc1nnc(-c2ncc(C(F)(F)F)cc2N2CCOCC2)o1]

* * * * *